United States Patent [19]

Cooper, Jr.

[11] Patent Number: 4,887,106
[45] Date of Patent: Dec. 12, 1989

[54] METHOD AND APPARATUS FOR PHOTOGRAPHIC ANALYSIS OF DENTAL RESTORATIONS

[76] Inventor: Henry H. Cooper, Jr., 8 E. 93rd St., New York, N.Y. 10128

[21] Appl. No.: 299,697

[22] Filed: Jan. 23, 1989

[51] Int. Cl.⁴ ............................................. G03B 29/00
[52] U.S. Cl. ...................................... 354/62; 354/132; 354/290
[58] Field of Search ...................... 354/62, 80, 132, 290

[56] References Cited

U.S. PATENT DOCUMENTS 3,971,954 7/1976 Kleinberg et al. ................. 354/62 X
4,123,768 10/1978 Kilshaw et al. .................... 354/80 X

OTHER PUBLICATIONS

"Dental Radiography and Photography", vol. 31, No. 3, Eastman Kodak Co., 1958.

Primary Examiner—L. T. Hix
Assistant Examiner—Brian W. Brown
Attorney, Agent, or Firm—Wolder, Gross & Yavner

[57] ABSTRACT

An apparatus for the recordation of images indicating the location of dental restorations in the mouth of an individual comprises support and positioning means for the person whose dental features are to be recorded, a first source of ultraviolet light located and arranged to illuminate the mouth area of the patient, a second source of visible light located and arranged to illuminate at least the face area of the patient, and a camera located and positioned to take a photograph of at least the mouth area while at least the face area is illuminated by the light sources. The intensity of the light sources may be adjustable to provide an accurate rendering of flesh tones while accentuating the restorations.

5 Claims, 2 Drawing Sheets

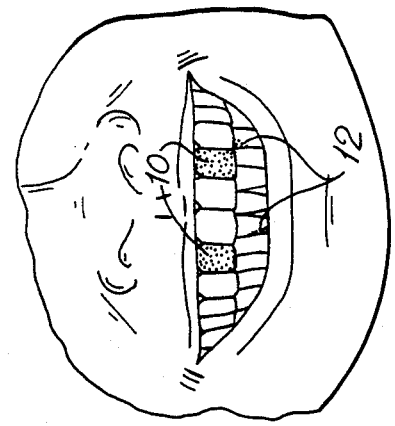
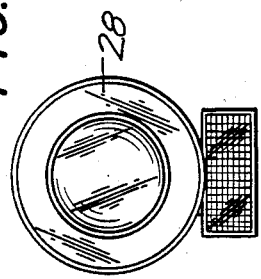
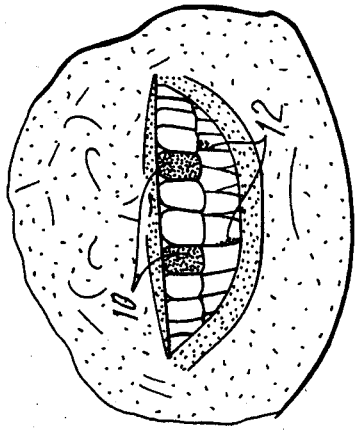
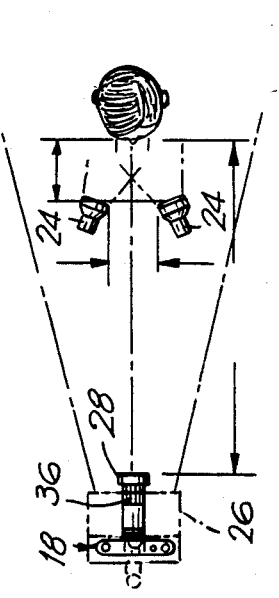
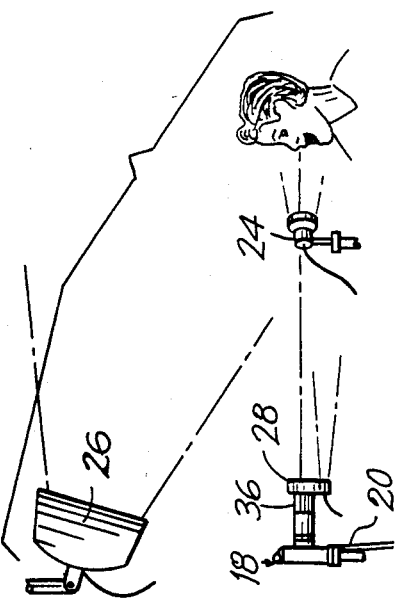

METHOD AND APPARATUS FOR PHOTOGRAPHIC ANALYSIS OF DENTAL RESTORATIONS

The present invention relates to the dental arts and, in particular, to a new and improved method and apparatus for providing an analysis of the optical photographic effects produced by dentures and other dental restorations in the mouth of an individual.

BACKGROUND OF THE INVENTION

Modern dental technology and procedures have progressed to the stage where fillings, crowns, bridges and other restorations, when in place in the mouth, normally maintain a completely natural appearance, blending with the patient's natural teeth in a non-obtrusive fashion. Notwithstanding the generally acceptable look of such structures, there is often an unacceptable difference between the look of such reconstructions and natural teeth when seen in photographs, motion pictures, and in certain other situations. It has been determined by the present inventor that such differentiation occurs as a result of the different reaction to ultraviolet light between natural teeth and many of the materials utilized in the construction of prosthetics, such that under certain lighting conditions such a porcelain restoration appears with a slight discoloration to a substantially dark appearance, depending on the specific lighting condition encountered. Often, the wearer of the restoration is unaware of the potential problem, and it is only after a photograph, film or the like is made, that the realization is achieved that the restorations stand out in great contrast to the natural teeth.

It is accordingly the purpose of the present invention to provide a method and apparatus by which such differences can be evidenced and recorded within a dental office to use as a demonstration and teaching tool with regard to corrective and restorative procedures utilized therein.

BRIEF DESCRIPTION OF THE INVENTION

In accordance with the stated and other objects, the present invention consists of the bathing of the mouth area with a combination of visible and ultraviolet light chosen to emphasize the differing florescence values of other porcelain restorative materials and natural teeth, while maintaining a proper light balance to properly present the flesh tones of the subject. While the mouth is bathed with such light a photograph is taken, the photograph serving as documentary evidence of the light effects upon the patient, whereby appropriate procedures, themselves not within the scope of the present invention, may be utilized to provide a more natural appearance to restorations under a wide variety of lighting conditions.

BRIEF DESCRIPTION OF THE DRAWINGS

A fuller understanding of the present invention will be accomplished upon consideration of the following detailed description of a preferred, but nonetheless illustrative embodiment of the present invention when taken in conjunction with the annexed drawings, wherein:

FIG. 2 is an elevation view taken along line 2—2 of FIG. 1 depicting the ring-flash portion of the present invention;

FIG. 3 is a top plan view of the apparatus of the invention;

FIG. 4 is a side elevation view of the apparatus of the present invention;

FIG. 5 is a representation of a photographic image created by the present invention in which conventional restorations appear in the patient's mouth; and FIG. 6 is a representation of a photographic image taken solely under ultraviolet light.

DESCRIPTION OF A PREFERRED EMBODIMENT

Figure 1:
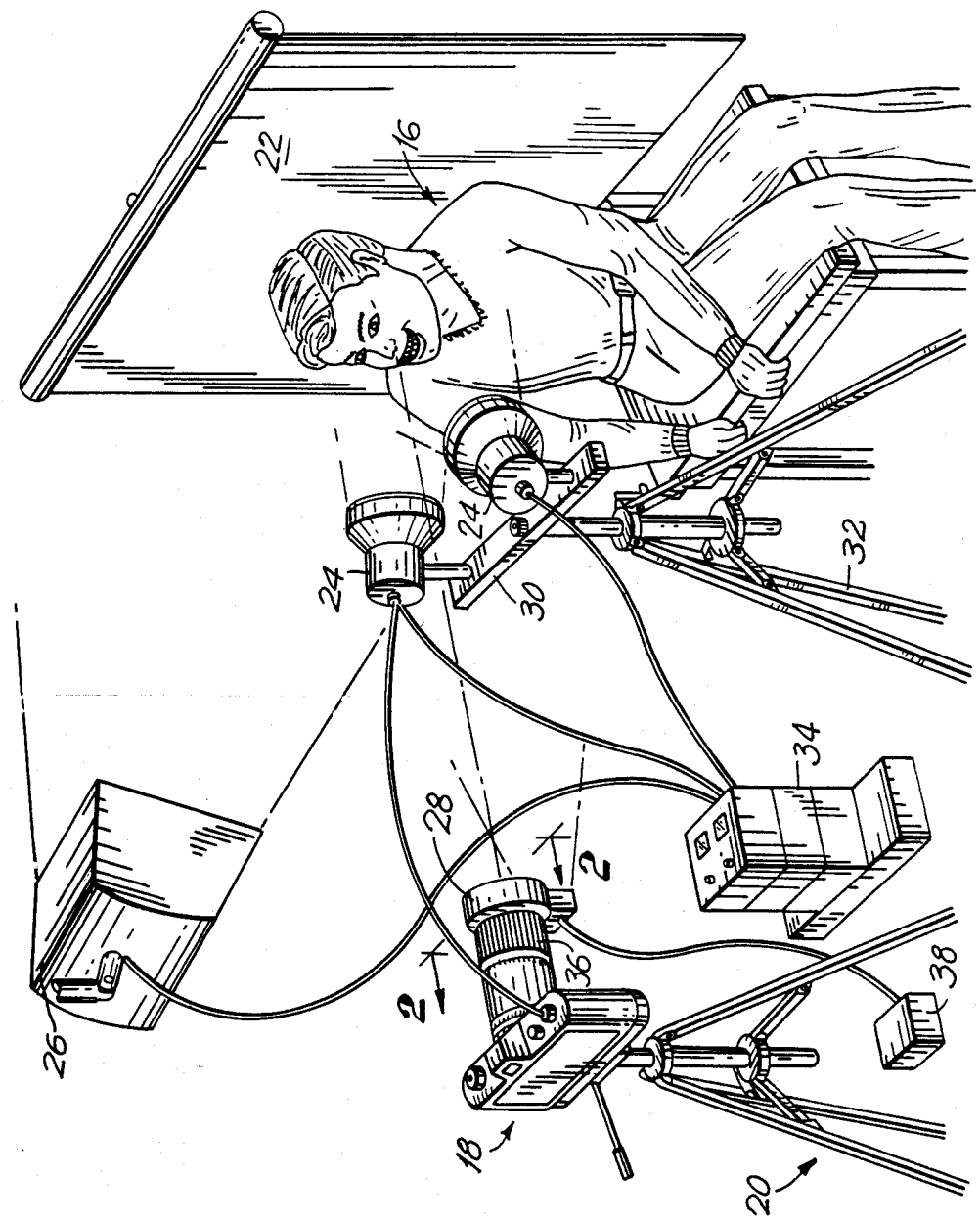
FIG. 1 is a perspective view of the apparatus of the present invention in position to record the mouth structure of an individual.

With reference to the Figures, the present invention is premised on the previously unknown and undiscovered determination that, under certain combinations of ultraviolet and visible light, conventional porcelain dentalwork, such as crowns, bridges and fillings, can appear, especially in pictures, as highly visible blemishes or discolorations, with the flesh and surrounding areas appearing normal. As such discolorations are not always apparent, a patient having porcelain dentalwork is often unaware of the detrimental effects such work has to his or her appearance until presented with a photograph or the like in which his or her appearance detrimentally reflects such shortcomings. In order to provide the practitioner and the patient a before-and-after record of the deficiency, and to assist the dental practitioner in locating such dentalwork preparatory to correcting such a deficiency, the apparatus illustrated in FIGS. 1 through 4 yields the type of image depicted in FIG. 5, in which dental caps 10 and fillings 12 in the natural teeth 14 of patient 16 clearly appear as darkened blemishes, while the patient's face and natural teeth appear in a more normal tonal composition. These results are to be compared to the representation of FIG. 6, which corresponds to a photograph taken under long wave ultraviolet light having a wavelength of 365 nm. As seen, the caps and fillings 10, 12 shown in FIG. 6 have more of a contrast to the natural teeth 14, and overall the face of the patient 16 is dark, thus maximizing the difference between the natural teeth and the restoration. Although the fluorescent contrast of the teeth is greater, the likelihood of one being present or photographed in such intense ultraviolet light is minimal. In addition, as the flesh is not reproduced in a lifelike manner, such photographs are of limited instructional value for the patient.

As seen in FIGS. 1 through 4, camera 18, which may be of the conventional 35 mm format, is mounted on tripod 20 in a straight-line alignment with the mouth of the patient 16. A non-glare screen 22 may be placed behind the patient for contrast purposes. The camera may utilize any of a variety of commonly available color films, such as Ectachrome 400 speed film manufactured and distributed by Kodak. The camera may be further provided with a lens especially adapted for relatively closeup photographs (a "macro" lens) as known in the art.

To provide the necessary combination of visible and ultraviolet light, a group of light sources 24–28 are employed. In particular, flash heads 24 are mounted to a flash bar 30 on tripod 32, approximately 4 inches apart, 6 inches from the patient's teeth. Each of the flash heads is angled to project directly upon the teeth. The flash heads may advantageously be part of a Lymedyne System 244 lighting system, which includes a power supply 34 and the facility for adjusting the light output of the individual light-emitting units connected thereto. Each of the flash heads 24 are provided with an appropriate filter to allow the passage of ultraviolet light of 365 nm wavelength. In particular, a Balcar "black light filter" may be employed. A light box 26 also controlled by the Lymedyne 244 unit, provides general visible illumination and is located above the patient's face, approximately 30 inches above and in front of the face. The output for the flash units 24 may be 400 watts, yielding a light meter reading between 11 and 16 for the 400 speed film, with a 1/60 sec. exposure. The light box output may be set at 200 watts. If the light meter reading of the patient's face is above 22, the output may be dropped to 100 watts.

The third source of light is ring-flash 28, which is mounted on the camera about macro lens 36. The ring-flash 28 is normally provided with its own power supply 38, and is synchronized with the exposure, as are flashes 24 and light box 26. Output for the ring-flash 28 should be such that of a light meter reading of 16. The output may be adjusted by controlling the power supply 36 output to the flash unit.

With the apparatus set up as described, a photographic image of the patient's face and mouth developed in the normal manner will result in an image in which the natural teeth fluoresce whitish, while non-florescent restorations are significantly dark. The gum and skin tones appear natural in color, thus providing a more realistic indication of the possible shortcomings of the restoration work under photographic and other conditions. This allows both the dental practitioner, as well as the patient, to be aware of potential shortcomings of the dentalwork and allows such restorations to be identified and modified to present a more acceptable result under critical lighting conditions.

I claim:

1. An apparatus for the recordation of images indicating the location of dental restorations in the mouth of an individual, comprising support and positioning means for the person whose dental features are to be recorded; a first source of ultraviolet light located and arranged to illuminate the mouth area of the patient; means for adjusting the light output of said ultraviolet light source; a second source of visible light located and arranged to illuminate at least the face area of the patient; means for adjusting the light output of said second visible light source; and camera means located and positioned to take a photograph of at least said mouth area while at least said face area is illuminated by said first and second light sources.

2. The apparatus of claim 1, wherein said first source of ultraviolet light comprises a pair of ultraviolet flash units spaced equidistant from the patient on opposite sides of the line between the camera and the patient.

3. The apparatus of claim 2, wherein said second source of visible light includes a light box and a ring-flash unit.

4. The apparatus of claim 3, wherein said ring-flash, light box and ultraviolet flash units are synchronized to the exposure of the film.

5. A method for producing an image of at least the mouth and face area of a patient whereby non-florescing dental reconstructions are highlighted and the remainder of the patient's face appearing in the picture appears in true color, comprising the steps of
 (i) positioning the patient before a camera;
 (ii) locating a first source of ultraviolet light to bathe the mouth area of the patient in such ultraviolet light;
 (iii) locating a second source of visible light such that at least the face portion of the patient is bathed in such visible light; and
 (iv) exposing a section of film such that the latent image carried thereon is as a result of both the effects of said visible and ultraviolet light upon the patient.

* * * * *